United States Patent [19]

Appleford et al.

[11] B 3,991,619

[45] Nov. 16, 1976

[54] APPARATUS FOR MEASURING SPECIFIC GRAVITY

[75] Inventors: David Dale Appleford, Swindon, England; David Philip King, Akron, Ohio

[73] Assignee: Monsanto Chemicals Limited, London, England

[22] Filed: Nov. 29, 1974

[21] Appl. No.: 528,401

[44] Published under the second Trial Voluntary Protest Program on February 3, 1976 as document No. B 528,401.

[30] Foreign Application Priority Data

Nov. 28, 1973 United Kingdom............... 55075/73

[52] U.S. Cl.................................. 73/437; 177/145; 198/339; 198/504; 214/2
[51] Int. Cl.²........................................... G01N 9/08
[58] Field of Search.............. 73/421 R, 432 R, 437; 177/145, 207; 198/19, 39; 214/2

[56] References Cited
UNITED STATES PATENTS

| | | | |
|---|---|---|---|
| 2,623,636 | 12/1952 | Pounds | 73/432 |
| 2,650,494 | 9/1953 | Linhorst | 73/437 |
| 3,380,597 | 4/1968 | Czetli | 214/2 |
| 3,730,364 | 5/1973 | Nakamura et al. | 198/19 X |
| 3,747,416 | 7/1973 | Wommack | 73/437 |

*Primary Examiner*—Herbert Goldstein

[57] ABSTRACT

An apparatus is provided for determining the specific gravity of a plurality of samples of solid water-insoluble materials which apparatus comprises a means for storing samples in spaced relationship, a means for weighing samples first in air and then in water, and a means for transferring samples, one at a time, from storage to the weighing means and returning each sample to storage after the weighing is completed, in which the transfer means and weighing means retain the same relative positions but the storage means and transfer means are movable so that the transfer means selects and transfers each sample in turn to the weighing means.

6 Claims, 6 Drawing Figures

3,991,619

APPARATUS FOR MEASURING SPECIFIC GRAVITY

This invention relates to automatic apparatus for determining the specific gravity of water-insoluble solids, in particular the specific gravity of water-insoluble solids such as plastics and rubber.

BACKGROUND OF THE INVENTION

The rubber industry has long used the measurement of specific gravity as a means of quality control. Typical conventional methods of measurement involve manual operations and visual observations by a laboratory technician, and are time-consuming, especially if data are required on a large number of samples.

Such data can be acquired much more rapidly by means of the apparatus of the present invention.

SUMMARY OF THE INVENTION

The invention provides apparatus for determining the specific gravity of each of a plurality of samples of a solid water-insoluble material, the apparatus comprising a rack for accommodating the samples in mutually spaced relationship, a weight-sensing assembly by means of which the sample can be weighed first in air and then in water, and a transfer mechanism for transferring the samples, one at a time, from the rack to the weight-sensing assembly and returning each sample to the rack after the weighings on that sample are completed, and wherein the transfer mechanism and the weight-sensing assembly retain the same relative positions but the rack and the transfer mechanism are relatively moveable so that the transfer mechanism can select each sample in turn for transfer to the weight-sensing assembly.

In a preferred form of the apparatus, the transfer mechanism comprises an arm having gripping means at one end, the said gripping means being operable into and out of gripping relationship with a sample, and the arm being pivoted to swing, preferably in a vertical plane, about an axis spaced from the said end, between the rack and the weight-sensing assembly.

In one embodiment, the arm comprises a cylinder with suitable ports, and an associated piston and piston rod, wherein an extension of the piston rod outside the cylinder is adapted to reciprocate between a forward and a retracted position, and the gripping means comprise two leaf springs, located one on each side, and extending beyond the forward end of the cylinder, and shaped so as to be urged towards mutual contact, the arrangement being such that in its forward position the piston rod extension lies between the leaf springs adjacent the forward end of the cylinder thereby holding the free ends of the springs apart by a distance sufficient to accommodate a sample between them.

BRIEF DESCRIPTION OF THE DRAWINGS

The invention is illustrated by the apparatus shown in the accompanying drawings, in which.

DESCRIPTION OF PREFERRED EMBODIMENTS

Figure 1:
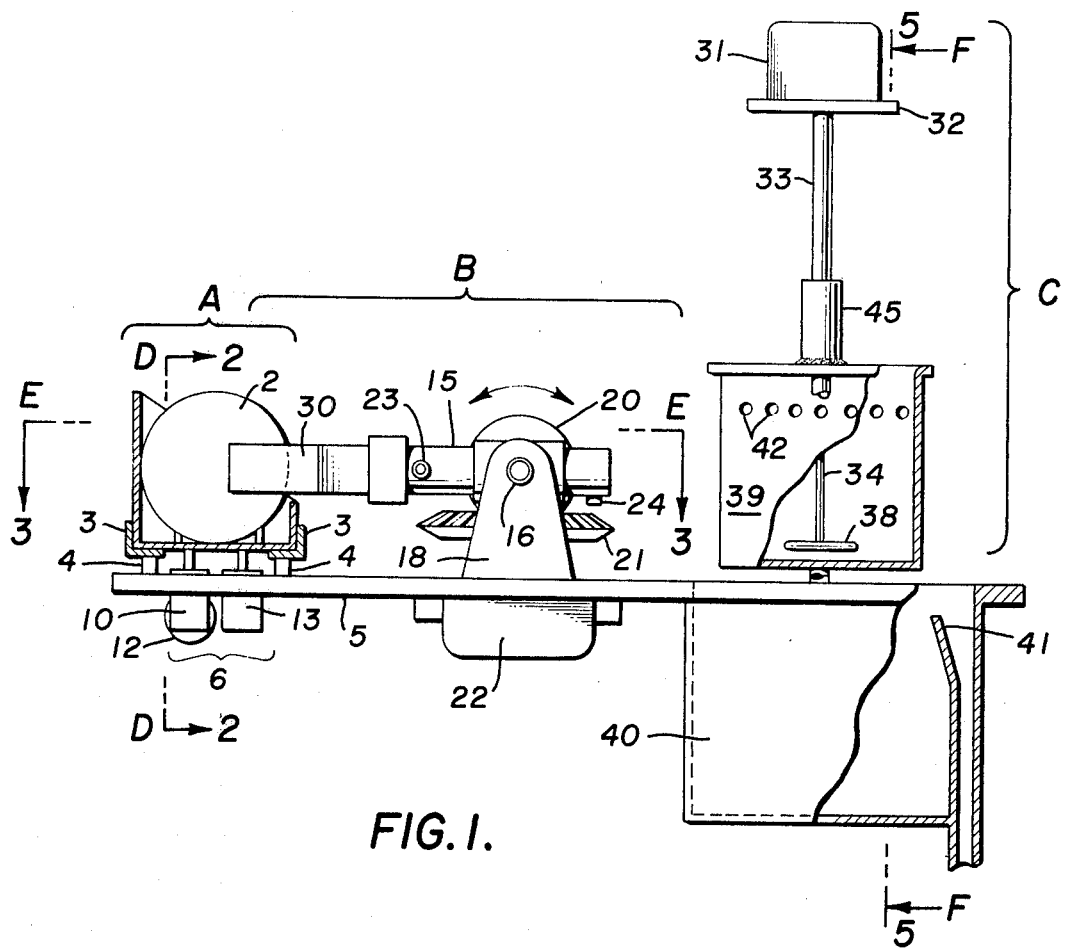
FIG. 1 is a side elevation, with certain parts in section, and with the rack, transfer mechanism and weight-sensing assembly indicated generally by the letters A, B and C respectively.
Figure 2:
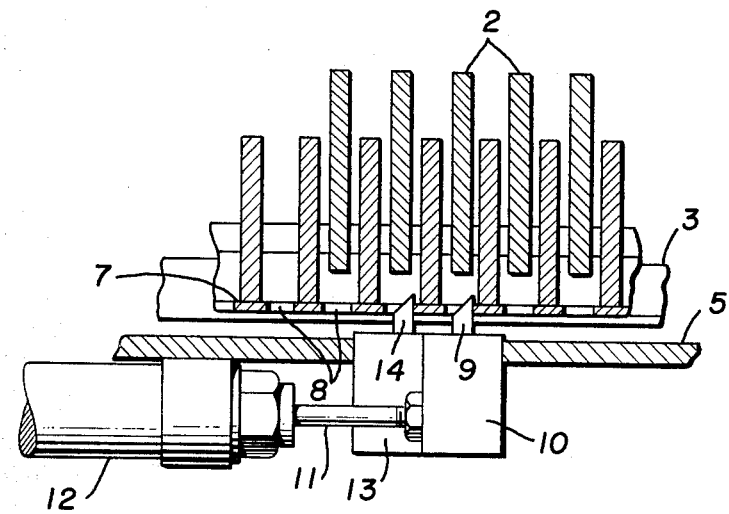
FIG. 2 is a section, on the line D—D of FIG. 1, of the rack and its associated advance mechanism.

Referring to FIG. 1, the rack 1 is designed to hold a row of disc or plate-shaped samples 2 facing the transfer mechanism edgeways. The rack is slidable on angled supports 3 attached through spacers 4 to a base plate 5. A slot in the base plate accommodates a rack advance mechanism 6 which is better illustrated in FIG. 2. FIG. 2 shows the base 7 of the rack formed with a series of slots 8 adapted for engagement with a spring-loaded pawl 9 (the loading being vertically upwards) having its lower end slidably housed in a recess in a block 10. The block 10 is screwed to the outer end of a piston rod 11 which is associated, for effecting reciprocatory motion of the block between a retracted and a forward position, with a cylinder 12 and a piston (not shown) within the cylinder. A stationary block 13, attached to the side of the slot in the base plate, is provided with a spring-loaded pawl 14 similar to the pawl 9, and is located such that the distance apart of the pawls when the block 10 is at its furthermost forward position is equal to the spacing between adjacent slots. This stationary block 13 prevents backwards movement of the rack when the block 10 retracts.

Figure 3:
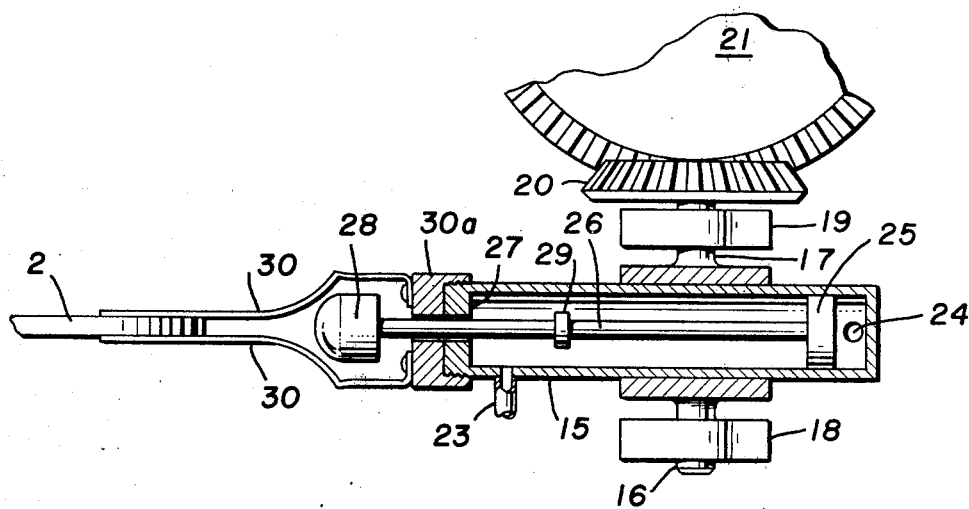
FIG. 3 is a plan view, partly in section, of the transfer mechanism in the direction E—E of FIG. 1, of the transfer mechanism.

With reference to FIGS. 1 and 3, the transfer mechanism comprises a cylinder 15 mounted for oscillatory motion about a transverse axis by means of stub axles 16 and 17 which are fixed on opposite sides of the outer wall of the cylinder 15. The axles are journalled in bearing plates 18 and 19 located on opposite sides of a slot (not shown) in the base plate 5. The axle 17 carries a bevel gear wheel 20 at its outer end. This wheel engages with a horizontal bevel gear wheel 21 having twice as many teeth as the wheel 20, and which is fixed to a vertical shaft driven by a 90° rotary actuator mechanism 22 located on the underside of the base plate 5.

Figure 4:
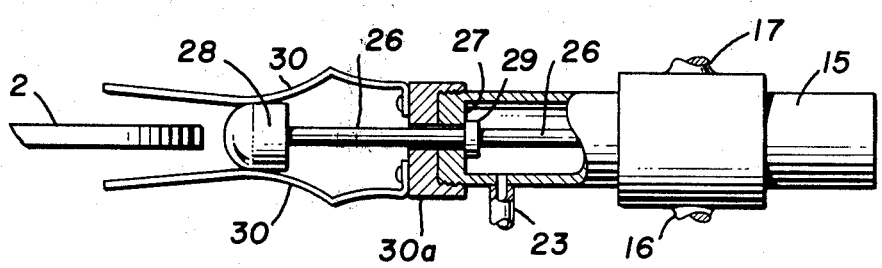
FIG. 4 is a plan view of part of the transfer mechanism.

The cylinder 15 has ports 23, and 24 a piston 25, and piston rod 26 which extends through a gland in the forward end wall 27 of the cylinder. At its extremity outside the barrel, the piston rod 26 carries a dome-shaped head element 28 having a diameter approximately the same as the internal diameter of the barrel. The arrangement is such that the head element 28 is adapted to occupy a retracted position as shown in FIG. 3, or a forward position as shown in FIG. 4. The travel of the head element in the forward direction is limited by abutment of a stop member 29 against the inner face of the wall 27.

The head element 28 cooperates with sample-gripping means formed by two leaf springs 30 which are pinned at their inner ends to opposite sides of the front face of a gland nut 30a, and are shaped to have forward portions which are urged into mutual convergence. As can be seen in FIG. 4, when the head element occupies its forward position, the leaf springs are held apart in an open position in which a sample can be accommodated between the free ends of the springs.

Figure 5:
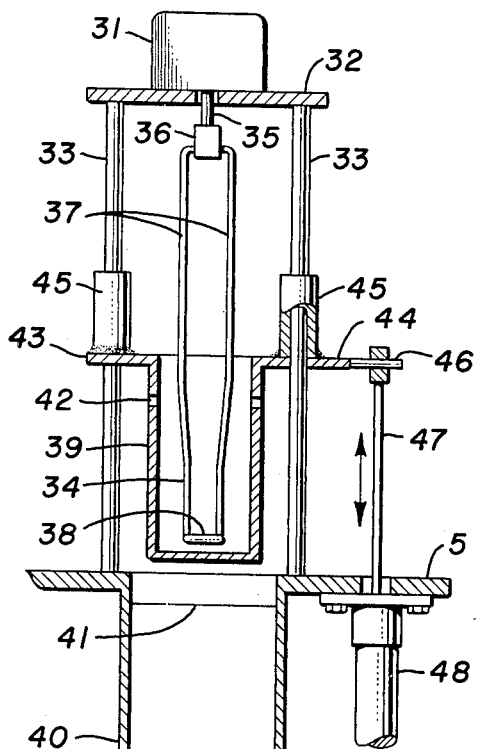
FIG. 5 is a section, on the line F—F of FIG. 1, of the weight sensing assembly.

The weight-sensing assembly illustrated in FIGS. 1 and 5 comprises a load cell 31 situated on a platform 32 supported by pillars 33. A wire framework sample hanger 34 is suspended from the load cell via a rod 35, which passes through an opening in the platform, and a block 36. The hanger comprises side members 37, the upper ends of which are directed inwardly for reception in opposite ends of a diagonal bore through the block, while the lower ends are attached to the midpoints of the longer sides of a rectangular loop 38. The loop is disposed substantially horizontally, and its size is such that a sample is supported on the shorter sides of the rectangle with a small segment of the sample below the loop.

The weight-sensing assembly includes an inner reservoir 39 adapted to occupy an upper position (as shown in FIGS. 1 and 5) in which it surrounds the lower end of the sample hanger, or a lower position in which it is situated within an outer reservoir 40. The outer reservoir is located beneath the base plate, which has a suitable cut-out to allow passage of the inner reservoir. The outer reservoir is provided with inlet means for water and a weir 41 for maintaining a constant level of water in the reservoir. A series of holes 42 in the side walls of the inner reservoir allows passage of water from the outer to the inner reservoir when the inner reservoir is in the lower position, and draining of the water in the inner reservoir to a fixed level when the inner reservoir is raised and water displaced by the sample hanger.

The upper ends of the walls of the inner reservoir are flanged at 43 and 44 adjacent to and outwardly beyond the pillars 33, the pillars passing through openings in the flanges. A sleeve 45 which is a sliding fit on the pillar is fixed to each flange. The flange 44 extends into an arm 46 which engages with one end of a piston rod 47. The rod, passing through an opening in the base plate, is actuated by a pneumatic cylinder 48 mounted vertically beneath the base plate.

Cylinders 12, 15 and 48, and the rotary actuator 22 have inlet and outlet ports and are connected to a compressed air supply on a series of parallel circuits, each circuit being controlled by a two-way, three-port valve. The valves can be mechanically or solenoid operated, and the required sequence of opening and closing the valves can be timed mechanically or electronically. A convenient arrangement is the use of solenoid-operated valves in conjunction with cam-operated electrical switches.

Figure 6:
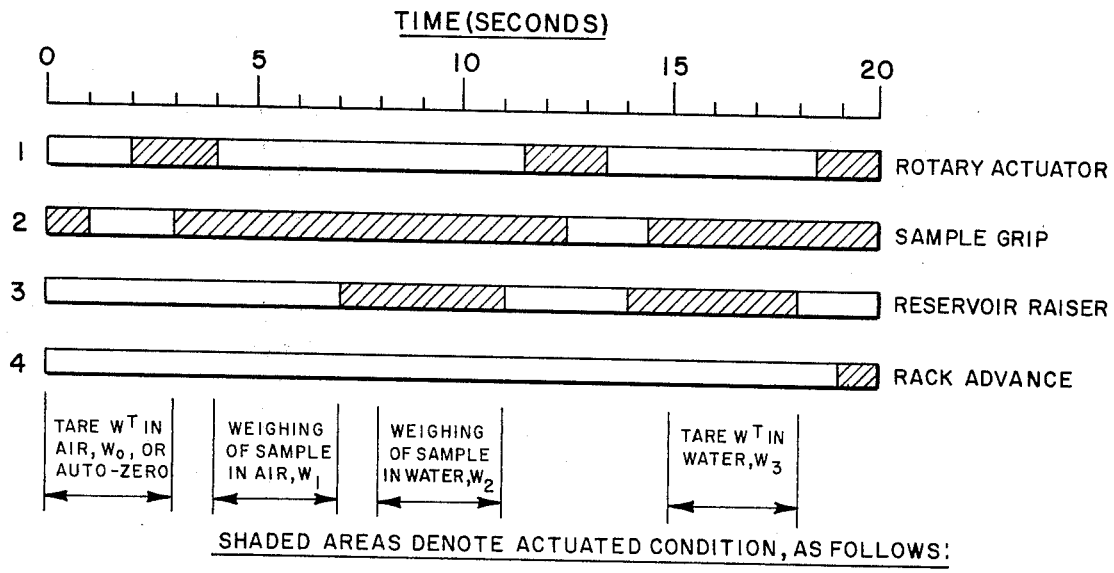
FIG. 6 is a diagram of the sequence of operations of the apparatus.

The cycle of operations for the determination of the specific gravity of each of a batch of samples can best be understood by reference to FIG. 6. At the beginning of a cycle, the leaf springs of the sample grip are open, one on each side of a sample in the rack, and the inner reservoir is in the lower position. At 1 second, the head element is retracted, thus causing the sample to be gripped between the leaf springs. At 2 seconds, air is admitted to the rotary actuator, thereby swinging the barrel of the transfer mechanism through 180° and bringing the sample to rest within the hanger 34 of the weight-sensing device. At 3 seconds, the sample is released to rest on the loop 38, and at 4 seconds the transfer mechanism swings back to park over the vacant space in the rack from which the sample was taken. During the period 0–3 seconds, the signal from the load cell indicates the tare weight in air of the hanger. During the period 3–7 seconds, the signal from the load cell indicates the increase due to the sample supported in the hanger, i.e., the weight of the sample in air.

At 7 seconds, actuation of the cylinder 47 raises the inner reservoir to immerse the sample in water, and during the period 8–11 seconds, the signal from the load cell indicates the weight of the sample plus hanger in water. At 11 seconds, the inner reservoir is lowered. At 11.5 seconds, air is admitted to the rotary actuator so that the transfer mechanism returns, at 12.5 seconds the sample is gripped, and at 13.5 seconds, the transfer mechanism swings back to the rack, where at 14.5 seconds, the grip opens to replace the sample in the rack. At 14 seconds, during the swing of the transfer mechanism, the inner reservoir is again raised, thereby immersing the loop and lower parts of the hanger, and during the period 15–18 seconds, the load cell indicates the tare weight of this system in water. The inner reservoir is lowered at 18 seconds. At 18.5 seconds, actuation of the rotary actuator swings the transfer mechanism away from the rack, at 19 seconds, the rack is advanced one position by the admission of air to cylinder 12, thus presenting the next sample for the transfer mechanism, which returns (with leaf springs open) at 20 seconds.

The specific gravity of the sample is derived from the various weighings taken during the sequence of operations, as follows:

If
$W_0$ = tare weight of hanger in air
$W_1$ = tare weight of hanger in air + sample weight in air
$W_2$ = tare weight of hanger in water + sample weight in water
$W_3$ = tare weight of hanger in water $$\text{Specific gravity} = \frac{W_1 - W_0}{(W_1 - W_0) - (W_2 - W_3)}$$

The load cell used in the weight-sensing device is preferably one having a low deflection, controlled to keep the natural frequency of the cell relatively high to reduce settling time (weighting time) to a minimum. Semiconductor strain gauges can be used to obtain a high output and linear characteristics, and temperature compensation networks can be incorporated to reduce zero drift.

The merits of the system are that the results are independent of the absolute accuracy of the load cell, since the relative weights in air and water are expressed as a ratio, and changes in accuracy during the very short weighing cycle can be neglected.

Other factors which could lead to incorrect values for specific gravity are the initial tare weight, (zero error) ($W_0$) and upthrust of water on weighing pan ($W_3$), these are measured and taken into account, ensuring that the true specific gravity value is obtained.

Variations on the apparatus described above include the use of a rotatable, circular rack driven continuously or intermittently by an electric motor through suitable gearing, and the use of an electric motor to drive the transfer mechanism.

The apparatus can be used in conjunction with an electronic program control and arithmetic processing and readout system, operating as follows:

The signal from the load cell is amplified, and fed to an analogue to digital converter, the output of which is in Binary Coded Decimal (B.C.D.) form. The logical sequence of operations is determined by the program control which provides timing pulses to the valves in the transfer mechanism, and to the appropriate logic circuits in the arithmetic system. The arithmetic operations are performed by a special integrated circuit, arithmetic processor which is programmed to evaluate the sample weight data and other factors.

A five line input is fed into the processor; four are for data or program numbers, and the fifth is a control line which is set to read 'data' or program instructions. The input of the processor has to be fed in 'bit' by 'bit', for both the data and program numbers. Multiplexing circuits are incorporated to enable these B.C.D. numbers to be sequentially presented to the input of the arithmetic processor.

The output of the processor is in serialized B.C.D. form and is fed into a store, and to a segmented numerical display. The display is blanked during the calculating and processing sequence and displays the final specific gravity value only. The final print out of specific gravity is taken from the output of the store.

The program sequence for performing the specific gravity calculation is as follows:

Basic Equation $$\frac{W_1 - W_0}{(W_1 - W_0)-(W_2 - W_3)} \quad \text{When } \begin{aligned} W_0 &= \text{tare weight} \\ W_1 &= \text{weight in air} \\ W_2 &= \text{weight in water} \\ W_3 &= \text{up thrust of weight pan} \end{aligned}$$

This is rearranged to correspond to the order in which data is received.

$$\frac{-W_0 + W_1}{-W_0 + W_1 - W_2 + W_3}$$

The data and program instructions are fed to the processor in the following order:
1. Enter instruction (−)
2. Enter data ($W_0$)
3. Enter instruction (+)
4. Enter data ($W_1$)
5. Enter instruction (−) and compute previous instruction $-W_0+W_1$ store value
6. Enter data ($W_2$)
7. Enter instruction (+) and compute previous instruction $-W_0+W_1-W_2$
8. Enter data ($W_3$)
9. Enter instruction (÷) and compute previous instruction $-W_0+W_1-W_2+W_3$
10. Re-enter data ($-W_0+W_1$)
11. Enter instruction 1/N and compute $$N = \frac{-W_0 + W_1 - W_2 + W_3}{-W_0 + W_1}$$

12. Enter instruction (=) and display specific gravity i.e., 1/N

Although the invention has been illustrated by typical examples, it is not limited thereto. Changes and modifications of the examples of the invention herein chosen for purposes of disclosure can be made which do not constitute departure from the spirit and scope of the invention.

The embodiments of the invention in which an exclusive property or privilege is claimed are defined as follows:

1. Apparatus for determining the specific gravity of each of a plurality of disc- or plate-shaped samples of a solid water-insoluble material, the apparatus comprising a rack movable in its longitudinal direction and having a plurality of transverse space members for accommodating samples in mutually spaced relationship wherein the gap between adjacent space members is sized to accept a disc- or plate-shaped sample inserted edgeways, a weight-sensing assembly by means of which the sample can be weighed first in air and then in water comprising a weight-sensing means with a sample receptacle suspended therefrom which sample receptacle includes a slot extending in the direction of the transfer mechanism adapted to receive a disc- or plate-shaped sample inserted edgeways and a reservoir operable between an upper position in which it surrounds the lower end of the sample receptacle and a lower position, and a transfer mechanism for transferring the samples, one at a time, from the rack to the weight-sensing assembly and returning each sample to the rack after the weighings on that sample are completed, comprising an arm having gripping means at one end which arm is pivoted to swing about an axis spaced from said end and pivots in a plane between the rack and the sample receptacle of the weight-sensing assembly, and wherein the transfer mechanism and the weight-sensing assembly retain the same relative positions but the rack and the transfer mechanism are relatively moveable from one to the next of a series of fixed relative positions so that the transfer mechanism can select each sample in turn for transfer to the weight-sensing assembly, and wherein in any fixed relative position of the rack and the transfer mechanism, the gap between two adjacent transverse spacer members of the rack, the arm of the transfer mechanism and the slot of the sample receptacle are substantially in alignment.

2. Apparatus according to claim 1 wherein the gripping means comprise leaf springs operable into and out of gripping relationship with a sample.

3. Apparatus according to claim 2 wherein the rack is substantially horizontal and the arm swings in a vertical plane.

4. Apparatus according to claim 2 wherein the arm comprises a cylinder having an associated piston and piston rod, an extension of the piston rod outside the cylinder is adapted to reciprocate between a forward and a retracted position, and the gripping means comprise two leaf springs, located one on each side of, and extending beyond the forward end of the cylinder, and shaped so as to be urged towards mutual contact, the arrangement being such that in its forward position the piston rod extension lies between the leaf springs adjacent the forward end of the cylinder thereby holding the free ends of the springs apart by a distance sufficient to accommodate a sample between them.

5. Apparaus according to claim 1 wherein the weight-sensing means is a load cell.

6. Apparatus according to claim 5 further including an amplifier for amplifying signals from the load cell, an analogue to digital converter adapted to receive signals from the amplifier, an arithmetic processor programmed to process data from the converter, automatic program control means for controlling the sequence of operations of the transfer mechanism and the sequence of operation of the arithmetic processor, and a read-out system arranged to accept the output from the processor, whereby the specific gravity of the sample is automatically recorded or displayed.

* * * * *